US006307120B1

(12) United States Patent
Glaug

(10) Patent No.: US 6,307,120 B1
(45) Date of Patent: Oct. 23, 2001

(54) CLOTH-LIKE, BREATHABLE DISPOSABLE ABSORBENT BRIEF WITH REFASTENING MEANS

(75) Inventor: Frank S. Glaug, Chester Springs, PA (US)

(73) Assignee: Confab Services AG (CH)

( * ) Notice: Subject to any disclaimer, the term of this patent is extended or adjusted under 35 U.S.C. 154(b) by 0 days.

(21) Appl. No.: 09/328,605

(22) Filed: Jun. 9, 1999

(51) Int. Cl.$^7$ .............................. A61F 13/66; A61F 13/15
(52) U.S. Cl. .................. 604/383; 604/389; 604/385.01; 604/385.31
(58) Field of Search ..................... 604/383, 389, 604/385.01, 385.31

(56) References Cited

U.S. PATENT DOCUMENTS

| | | | |
|---|---|---|---|
| 4,463,045 | 7/1984 | Ouellette et al. | 428/131 |
| 4,911,702 | 3/1990 | O'Leary et al. | 604/389 |
| 5,147,347 | * 9/1992 | Huang et al. | 604/390 |
| 5,176,672 | * 1/1993 | Bruemmer et al. | 604/385.1 |
| 5,558,658 | * 9/1996 | Menard et al. | 604/385.1 |
| 5,569,233 | 10/1996 | Gouliat | 604/391 |
| 5,624,427 | 4/1997 | Bergman et al. | 604/391 |
| 5,629,063 | 5/1997 | Gobran | 428/40.1 |
| 5,762,645 | 6/1998 | Allen et al. | 604/391 |
| 5,803,920 | * 9/1998 | Gilman | 604/378 |
| 5,810,797 | 9/1998 | Menard et al. | 604/378 |
| 5,904,673 | 5/1999 | Roe et al. | 604/385.2 |
| 6,191,055 | * 2/2001 | Boyer, III et al. | 442/80 |

FOREIGN PATENT DOCUMENTS

| | | | |
|---|---|---|---|
| 0800808 | 10/1997 | (EP) | A61F/13/62 |
| WO 98/35641 | 8/1998 | (WO) | A61F/13/56 |

* cited by examiner

*Primary Examiner*—John G. Weiss
*Assistant Examiner*—Michael Bogart
(74) *Attorney, Agent, or Firm*—Caesar, Rivise, Bernstein, Cohen & Pokotilow, Ltd.

(57) ABSTRACT

An adult brief garment for use in controlling incontinence is provided. The brief has a chassis which includes a front portion, back portion and an interposed crotch portion. The chassis consists of a fluid-impervious, cloth-like laminate along the central region of the chassis and hydrophobic, cloth-like, nonwoven side panels at each side of the central region. An liquid absorbent core is positioned over the central region. Plural fastening tapes are applied to the side panels at the back portion of the chassis. The front portion of the chassis includes soft, flexible landing zones for releasable receipt of the tapes to hold the brief in place. Each landing zone takes up a substantial portion of its associated side panel and contiguous portions of the central region of the chassis and each includes a myriad of small (e.g., micro-sized) apertures or holes therein for breathability, e.g., to allow moisture vapor to pass therethrough. The sides within the crotch section of the brief are elasticized to fit around the wearer's legs and prevent the egress of urine therefrom. The top or waist section of the front panel and the top or waist section of the back panel are also elasticized to hold the brief snugly about the waist of the wearer.

17 Claims, 2 Drawing Sheets

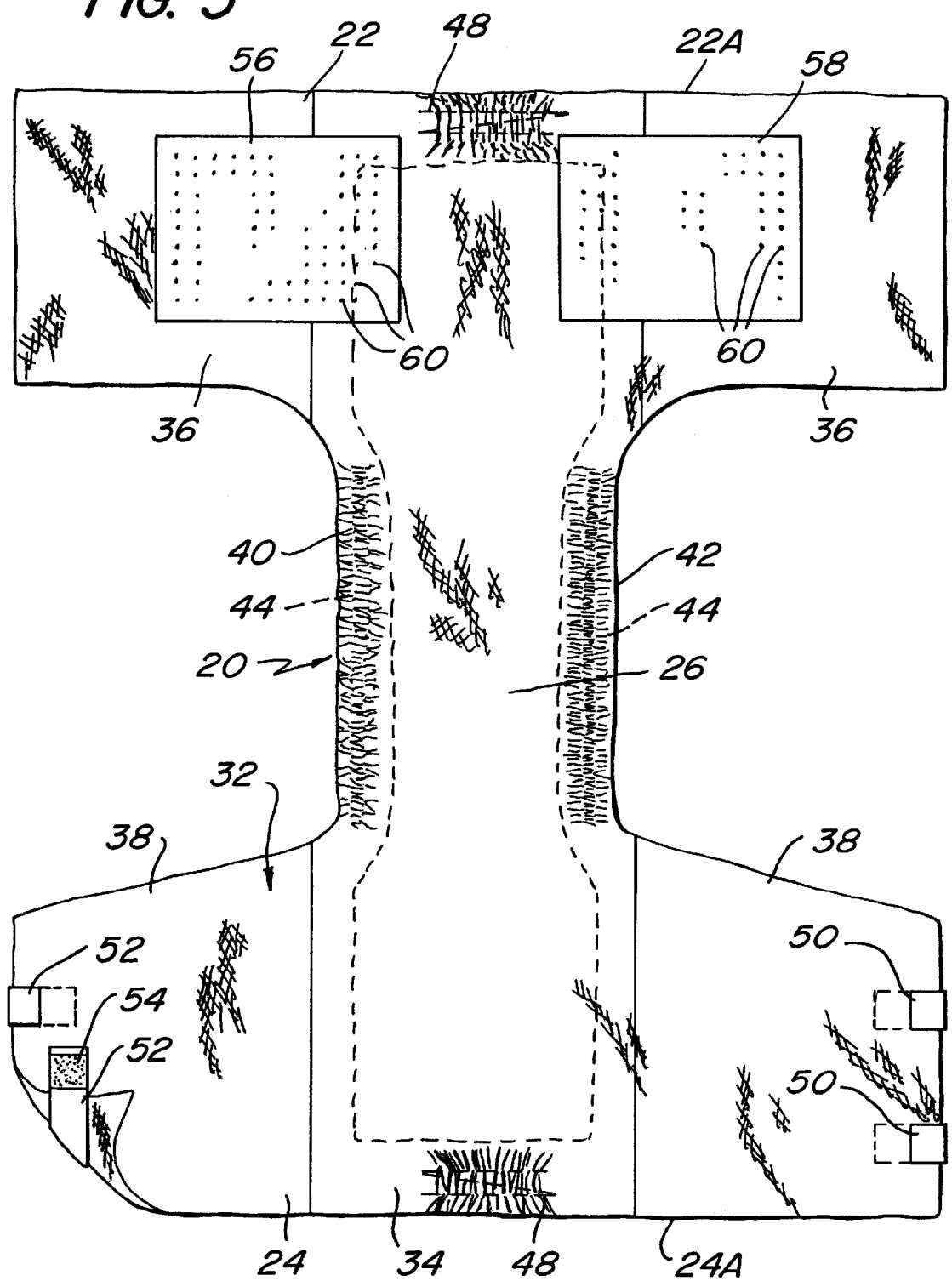

CLOTH-LIKE, BREATHABLE DISPOSABLE ABSORBENT BRIEF WITH REFASTENING MEANS

FIELD OF THE INVENTION

This invention relates generally to disposable absorbent articles, e.g., briefs for incontinent adults, and more specifically to disposable absorbent articles which exhibit cloth-like features for improved comfort and having re-fastenable fastening means enabling the articles to be put on to any desired fit, removed and put on again, as many times as desired.

BACKGROUND OF THE INVENTION

As populations continue to increase in longevity, incontinence, a problem of age presents a need for fluid control in undergarments. This challenge is being met adequately with a variety of disposable diaper designs. Never the less, certain deficiencies have been recognized in diapers that are currently found in the market place. For example many of them are thick and bulky, make noise during walking and of particular importance to the present invention is the fact that they tend to be hot and uncomfortable due to the inability of these garments to transmit moisture vapor to the outside. One solution that is currently available to solve this problem is the use of breathable diaper design that comprises a polymeric central region (longitudinal direction) that provides the inherent ability to stop the flow of fluid from the diaper and nonwoven cloth-like sides which allow passage of air and moisture vapor quite readily.

One of the most important components of a disposable diaper or brief is the method of attaching the two side panels to form the three dimensional garment. A popular method of achieving this attachment is to fix pressure sensitive tapes on the nonwoven side panels attached to the rear of the diaper or brief. When putting the garment on, these pressure sensitive tapes are attached to the nonwoven side panels which extend from the front of the garment. This method is low in cost and is adequate for forming a tight, strong closure. However, the major disadvantage is that once the adhesive is pulled away in order to remove the garment, the closure cannot be used again.

In recent years a refastenable attachment has been developed whereby a plastic film (sometimes called a "landing zone") is attached to the nonwoven on the face that receives the adhesive tape. This film has a releasable surface allowing the adhesive tape to be attached and released through several cycles. Such a refastenable closure systems has gained wide acceptance in adult incontinence disposable diapers and briefs. Unfortunately, plastic films with releasable surface properties, such as, for example film of polyethylene terephthalate, are not permeable to moisture vapor and air, thereby reducing the overall comfort of the garment incorporating such materials.

Adult incontinence represents a transition from underwear to the use of some type of absorbent article to be added to the underwear or to completely replace it. For light-to-moderate incontinence needs, absorbent pads, guards, shields or absorbent inserts which are used in conjunction with underwear have proven acceptable. For moderate-to-heavy incontinence needs, either belted undergarments or adult briefs have been used in place of underwear. While such briefs may be generally suitable for their intended purposes if they incorporate reusable fastening systems including landing zones formed of plastic materials having releasable surface properties, they leave much to be desired from the standpoint of comfort, e.g., they do not exhibit the level of comfort adults have become accustomed to from cloth undergarments. Thus, it had been believed that there is no solution to the problem of having a refastenable attachment system for an adult incontinent brief that allows the transmission of moisture vapor and air in order to improve comfort for the wearer.

OBJECTS OF THE INVENTION

It is a general object of this invention to provide a disposable absorbent garment which addresses the needs of the prior art.

It is another object of this invention to provide a disposable adult incontinent garment which includes reusable fastening means, yet which exhibits good breathability, e.g., the rapid transmission of air and/or moisture vapor through it.

It is still another object of this invention to provide a soft and flexible disposable adult incontinent garment which includes reusable fastening means.

It is still another object of this invention to provide a disposable adult incontinent garment which includes reusable fastening means, and which can be effectively fit onto the body of the wearer.

It is still another object of this invention to provide an adult incontinent garment having reusable fastening means and which provides a good visual appearance and a soft, flexible, cloth-like feel.

It is still another object of this invention to provide a disposable adult incontinent garment having reusable fastening means and which provides wearing comfort and quietness approaching that of a cloth undergarment.

SUMMARY OF THE INVENTION

A disposable absorbent article, e.g., an adult incontinent brief, which is arranged to be worn by a person to trap and collect liquid waste products. The article has a flexible chassis including a front portion, a crotch portion, and a back portion. The chassis has an absorbent layer for absorbing both liquid and solid waste materials.

The back portion of the article has at least one fastening tab projecting from each side. The front portion of the article has at least one landing zone formed of a moisture impervious, vapor pervious material to provide a release surface to which the tabs are arranged to be releasably secured to hold the article in place on the person. The landing zone includes a large plurality of small apertures therein to enable moisture vapor from within the article to pass therethrough.

In accordance with one preferred embodiment of the invention the article includes two landing zones and at least two adhesive tabs on each side of the back portion of the article. The tabs extends from a respective sides of the back portion. Each of the zones is located on the front portion and is adapted to releasably receive a respective one of the fastening tabs.

The body member basically comprises a outer cover (e.g., a soft non-woven hydrophobic material), an inner liner (e.g., a soft non-woven hydrophilic material), and the liquid absorbent core (e.g., cellulose pulp fibers and superabsorbent particles). The liquid absorbent core is interposed between the outer cover and the inner liner, which are bonded together.

DESCRIPTION OF THE DRAWING

FIG. 3 is a plan view of the garment shown in FIG. 1.

DETAILED DESCRIPTION OF THE PREFERRED EMBODIMENT

Figure 1:
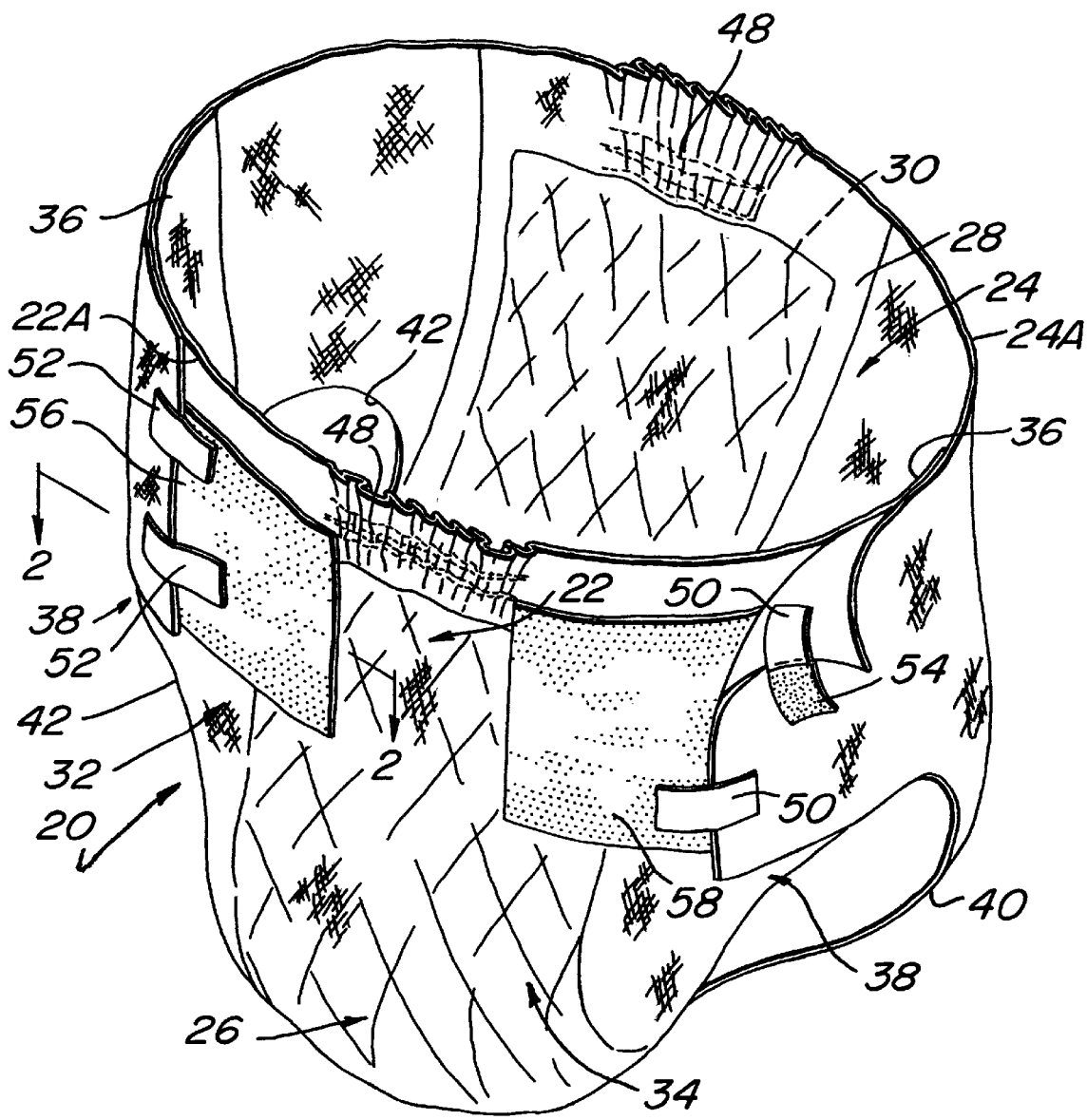
FIG. 1 is an isometric view of a cloth-like breathable disposable absorbent garment, e.g., a brief, constructed in accordance with this invention.
Figure 2:
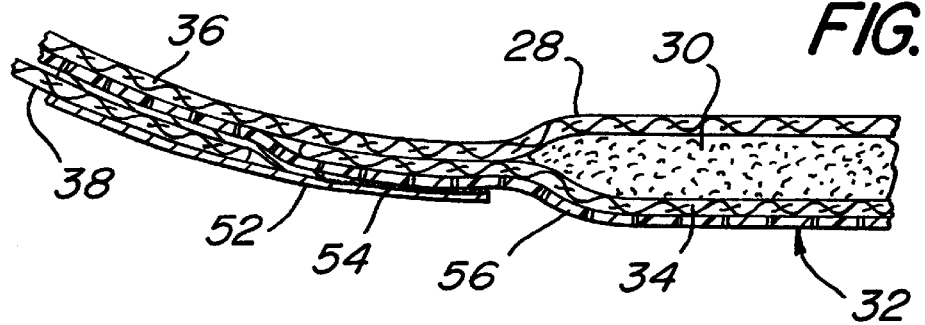
FIG. 2 is an enlarged sectional view taken along line 2—2 of FIG. 1.

Referring now to the various figures of the drawing wherein like reference characters refer to like parts, there is shown in FIG. 1 a disposable absorbent article 20 constructed in accordance with one embodiment of this invention. The article 20 of FIG. 1 is in the form of an adult incontinent brief which is cloth-like and breathable. While the following description will focus on adult incontinent briefs, it should be clear that the subject invention can be used for any type of absorbent article or garment to be worn by a person for trapping urine and having releasably securable fasteners to enable the article or garment to be put on and taken off repeatedly.

The brief 20 basically comprises a chassis made up of a front portion 22 in a front waist section, a back portion 24 terminating in a back waist section, and an intermediate crotch portion 26.

The chassis is formed of a liquid pervious inner layer 28, a liquid absorbent core 30, and an outer cover 32. The outer cover 32 is in turn made up of a liquid impervious center section 34, a front pair of cloth-like, breathable side panels 36, and a back pair of cloth-like, breathable side panels 38. The liquid impervious center section 34 of the outer cover 32 is rectangular in shape. The front side panels 36 are mirror images of each other and are bonded by any suitable means (such as adhesive, thermal or ultrasonic bonding) to the marginal edges of the center section at the front portion 22 of the brief so that they project outward therefrom. In a similar manner the backside panels 38 are mirror images of each other and are similarly bonded to the marginal edges of the center section at the back portion 24 of the brief so that they project outward therefrom. The resulting cover-stock is thus of a generally I-shape forming respective leg cut-out regions 40 and 42 on opposite sides of the crotch portion 26.

The side panels 36 and 38 of the brief 20 may be formed of any suitable cloth-like breathable material, e.g., woven or nonwoven materials or combination thereof. An example of a suitable material for the side panels 36 and 38 is a hydrophobic 30 gsm (grams per square meter) polypropylene spunbond available from PGI Nonwovens, Landisville, N.J.

The center section 34 of the outer cover-stock is a liquid-impervious laminate comprising a soft nonwoven (cloth-like/hydrophobic) on the outside and fluid-impervious film (low gauge poly) on the inside. An example of this is a poly laminate available from Clopay Plastic Products Company, Cincinnati, Ohio, which consists of 0.6 mil polyethylene film & 17 gsm SMS (spunbond/meltblown/spunbond) nonwoven. Another lower version is a poly laminate 9B-396 available from Huntsman Packaging, of Newport News, Va., which consists of 0.3 mil copolymer film & 14 gsm SBPP (spunbond polypropylene) nonwoven. However, other laminate variations may be used in various gages and basis weights. For instance, other polymers (polypropylene, olefins, polyester, co-extruded polymers, etc.) or coatings (adhesive, synthetic rubber, latex, polyurethane, etc.) can be used in place of the polyethylene film. Other material components (polypropylene, polyethylene, bi-component fibers, polyester, cotton, rayon, nylon, olefins, etc.) can be used in either woven or non-woven (spunbond, thermal bond, through-air bond, etc.) construction in place of the SMS outer cover. The preferred fluid-impervious film for the liquid-impervious laminate is a breathable 0.8 mil polyethylene version, which contains calcium carbonate, available from Exxon Chemicals, Lake Zurich, Ill. This material allows water vapor to pass through it, but does not permit the liquid itself to pass through it.

Each of the leg cut-out regions 40 and 42 is elasticized. To that end, an elastic adhesive, such as Hot Melt 70-4309 from National Starch and Chemical Company, Bridgewater, N.J., is intermittently applied to each outer edge of the poly-laminate center section 34 to secure plural elastic strands or threads 44 thereto. The elastic strands 44 may be of any suitable material. For example, one particularly suitable material is synthetic rubber, such as Lycra (Decitex 680) from E. I. DuPont DeNemours & Co., Wilmington, Del. Four such strands 44 are attached directly on the top surface of the elastic adhesive area on the center section 34 of the chassis while under tension (anywhere from 25–300% elongation). The inner liner 28 of the chassis is secured over the center section 34 (as will be described later) to sandwich the elastic strands 44 therebetween. When tension is released, the strands contract to gather up the leg openings 40 and 42 as shown in FIG. 3. It should be appreciated that any number and/or other elastomeric components (such as natural rubber, latex, polyurethane, Kraton film, Spandex, elastic foam, etc) may be used to elasticize the leg openings along the crotch region. Either slot coating, spiral spray, meltblown, or other adhesive application means may be used to secure the elastic strands 44 in place.

Each of the waist sections, i.e., the upper portion of the front section 22 contiguous with the top edge 22A and the upper portion of the back 24 section contiguous with the top edge 24A of the brief is also elasticized. To that end an elastic adhesive, such as Hot Melt 70-4309 from National Starch and Chemical Company, Bridgewater, N.J., is applied intermittently along the central region of the poly-laminate center section 34 of the outer cover 32 at both the front and back waist sections 22A and 24A, respectively, for securing an elastomeric strand 48 or thread thereto. In particular a continuous synthetic rubber strand 48, such as Lycra (Decitex 680) from E. I. DuPont DeNemours & Company, Wilmington, Del., is applied in a tensioned zig-zag pattern at both the central region of the front waist section 22A and the central region of the back waist section 24A. Construction adhesive, such as Hot Melt 70-4535 available from National Starch and Chemical Company, Bridgewater, N.J., used to hold the elastic strands in place between the center section 34 of the outer cover 32 and the inner layer 28 of the chassis. Either slot coating, spiral spray, meltblown, or other adhesive pattern application means may be used to secure the strands, as well as other adhesive formulations. When tension is relieved on the strands 48, the waist sections gather at the location of the strands as shown in FIGS. 1 and 3.

The absorbent core 30 is formed and attached directly on top of the center section 34 of the outer cover 32. As shown in FIG. 3 the core is of a generally "dog-bone" shape, but may be of any shape or contour desired, e.g., rectangular, triangular, trapezoid, T-shaped, or irregularly shaped. In the preferred embodiment shown herein, the core is made up mainly of cellulosic fibers, e.g., wood pulp fluff made up of bleached sulphate wood pulp containing softwood fibers, such as that available from International Paper, Tuxedo, N.Y., co-mingled with hydrogel polymer particulates (known as Super Absorbent Polymer or "SAP") such as cross-linked polyacrylate ASAP 2102 available from Chemdal Corporation, Palatine, Ill. These materials may be optionally enwrapped in tissue, e.g., 17.1 gsm tissue from Cellu Tissue Corporation, East Hartford, Conn. The amount of each absorbent material and SAP/fluff ratio depends on the size of the brief, e.g., "Small", "Medium", "Large" or "Extra Large" and whether or not a transfer layer or fluid acquisition layer component is included in the absorbent system. In this regard, a fluid-acquisition layer (not shown) may be provided between the absorbent core 30 and the topsheet 28. The fluid-acquisition layer serves to manage, transport, accommodate and/or direct high volumes and high flow rates of urine into the core. The fluid-acquisition layer can be a through-air bonded/carded web, a spun-bond bi-component non-woven web, a web of cross-linked cellulosic fibers, apertured 3D film or the like. One particular suitable material is available from PGI Nonwovens, Landisville, N.J., and has an overall basis weight of 40 gsm, with high denier (10 denier) bi-component fibers situated on the top (facing the topsheet) and low denier (6 denier) bi-component fibers situated on the bottom (facing the core). The bi-component fibers are made of a polypropylene inner core and polyethylene outer sheath. The fluid-acquisition layer may be adhesively secured in place by any suitable construction adhesive or hydrophillic adhesive, e.g,. Cycloflex adhesive available from National Starch and Chemical, Bridgewater, N.J. In the exemplary embodiment described above, 90 grams of fluff and 10 grams of SAP is used for the absorbent core for both the "Medium" and "Large" sizes of briefs with a transfer or acquisition layer, of 12.8 gsm/100 mm/polyester fibers adhered on top of the absorbent core in a "continuous" configuration. A higher basis weight transfer layer, e.g., 12–50 gsm, with a variety of fiber material combinations and deniers, can be also used. Other high-absorbency materials can also be used for the core, such as super absorbent fibers or peat moss.

If desired the core 30 may be held in place by a hydrophillic construction adhesive, such as Cycloflex from National Starch and Chemical Corporation, Bridgewater, N.J. In such an arrangement the adhesive may be applied on top of the transfer layer and absorbent core.

As best seen in FIG. 1, the topsheet or inner layer 28 is a rectangular panel formed of a moisture pervious material of approximately the same size and shape as the center section 34 of the outer cover 32. One particularly suitable material for the inner layer 28 is a 17 gsm wettable nonwoven coverstock, made of thermal bond polypropylene, available from PGI Nonwovens, Landisville, N.J. The inner layer 28 is attached directly ontop of the poly-laminate center section 34 completely around the perimeter of the absorbent core 30 by the adhesive as described earlier. The inner layer 28 may be formed of other material fibers (e.g., polyethylene, bi-component, polyester, rayon, cotton, etc.), fiber combinations (e.g., spunbond, air laid, wet laid, hydroentangled, etc.), and basis weights may be used as well.

If desired, in order to provide additional fluid containment along the crotch/leg cut-out region of the brief, standing leg or leak guards (not shown) may provided. To that end two lines of standing leak guards would be adhered on top of the inner surface of the topsheet 28 towards the outside of the leg elastic location. The leak guards may be of any suitable construction, e.g., a cloth-like/hydrophobic material composite containing two strands of elastic along the top section of the composite. One particularly suitable construction for the leak guards is a hydrophobic SMS (spunbond-meltblown-spunbond) nonwoven, e.g., 15 gsm, available from AVGOL, Holon, Israel, having elastic strands of Lycra Decitex 680, available from E. I DuPont DeNemours & Co., Wilmington, Del. The elastic strands are stretched, e.g., within the range of 25–300% elongation, and adhered longitudinally upon the SMS nonwoven, offset towards the top end. The top end of the SMS nonwoven is folded over the elastic strands to completely enclose them. The bottom section of the SMS nonwoven is adhered directly to the internal cover 28. The end result is an L-shape leak guard configuration, where the vertical side of the composite faces towards the inside of the brief. If desired, the elastic strands of the standing leak guards can be elastically functional in a continuous mode along the longitudinal direction of the brief.

The brief 20 is arranged to be held in place on the body of the wearer in a conventional manner, e.g., by respective pairs of fastening tabs or tapes 50 and 52 projecting outward from the back side panels 38. In accordance with one preferred embodiment two tabs 50 and 52 are used on each back side panel 38, with each tab being approximately 28.5 mm wide and available under the designation FT 4965 fastening tapes and RT 4929 release tapes from Avery Dennison, Painesville, Ohio. It should be appreciated that any number of tapes and tape sizes can be used. In any case, the underside of each tab includes pressure-sensitive adhesive surface 54 which is arranged to be releasably secured to respective "landing zones" (to be described hereinafter) on the front portion of the brief to hold the brief in place on the wearer, yet which can be disconnected therefrom many times, so that the brief may be taken off and then replaced as often as desired.

As should be appreciated by those skilled in the art, the ability to be able to disconnect and reconnect the fastening tapes so that the brief can be taken off and put back on as many times as desired is of considerable importance for adult incontinent briefs. In particular, it is quite common for a wearer of an unsoiled adult incontinent brief to desire to remove it in order to use the bathroom in a normal manner, and then to replace the unsoiled brief to provide protection from incontinence later. Since the size and shape of the lower torso of adults varies greatly, adult briefs have heretofore made use of large "landing zones" in the front of the brief for receipt of the tapes at any position on the zones, to enable the wearer to customize the fit of the brief to his/her particular anatomy. Moreover, as discussed earlier, landing zones of prior art briefs have typically been formed of materials exhibiting a release surface so that the fastening tapes can be repeatedly secured to them and unsecured from them without adversely affecting the adhesive qualities of the tapes. This type of landing zone construction, unfortunately, is moisture impervious and non-breathable so that its use significantly detracts from wearing comfort due to its propensity to trap moisture within the brief.

The brief 20 of this invention, in contradistinction, overcomes that disadvantage of the prior art by providing large, breathable landing zones for the fastening tapes 50 and 52 to releasably engage. In particular, the brief 20 makes use of two large landing zones 56 and 58. Each zone is of any suitable shape, e.g., rectangular, and is located covering a substantial portion of the side panels 36 and contiguous portions of the center section 34 of the outer cover which is interposed between those side panels in the front portion 22 of the brief 20. The landing zones 56 and 58 are located at a position so that when the brief 20 is folded in half with the front waist section disposed opposite the back waist section, the landing zones 56 and 58 will be aligned with the tape tabs 52 and 50, respectively.

As will be appreciated by those skilled in the art, when the brief 20 is in place on the wearer the front waist section is disposed over the wearer's lower abdomen region, the back waist section is disposed over the wearer's lower back and buttocks region, and the crotch portion is located between the wearer's legs. The fastening tabs 50 may then be brought into engagement with any portion of the landing zone 58, while the tabs 52 are brought into engagement with any portion of the landing zone 56, to releasably secure the tapes thereto so that the brief may be made as tight and conforming about the wearer's waist as the wearer desires.

In accordance with one preferred embodiment of this invention the landing zones 56 and 58 themselves are formed of soft, flexible adhesive tape sections which are fixedly secured onto the outer cover 32 of the brief 20, i.e., the outer surface of the side panels 36 and central section 34. In particular, two 6.5"×5.5" strips or sections of a fluid impervious film having an adhesive underside, such as KR0882 Tape available from 3M Corporation, Minneapolis, Minn. are cut and secured by the underside adhesive in position on the front portion of the brief slightly spaced apart from each other to form landing zones 56 and 58.

As should be appreciated by those skilled in the art any number of fastening tapes and any number of landing zones can be used. Moreover, other reusable "mechanical" fasteners can be used in lieu of adhesive tapes. For example, releasably securable hook and loop fastening systems can be used. To that end, the tabs 50 and 52 may be made of strips of a myriad of microhooks available from YKK (U.S.A.), Inc., Macon, Ga. and the landing zones may be adhesively secured patches of cooperating multi-loop material arranged to releasably receive the microhooks. Such multi-loop material is available from Guilford Mills, New York, N.Y.

In any case the material, e.g., the fluid-impervious film of the tape or the fluid-impervious backing of the multi-loop patches, making up the landing zones 56 and 56 is perforated across its entire expanse to form a myriad of very small, e.g., 0.03" (0.76 mm) diameter, holes or apertures 60 in a staggered pattern spaced from one another by approximately 5 mm and through which moisture from the interior of the brief may pass. The inclusion of the apertures or holes 60 enables the landing zones 56 and 58 to exhibit very good moisture transmission properties, e.g., a rate of air flow per unit area within the range of approximately 10 m3/m2.s and up to approximately 80 m3/m2.s for high basis weight SBPP (spunbond polypropylene) and SMS (spunbond/meltblown/spunbond) nonwovens making up the brief's chassis.

As should be appreciated from the foregoing the briefs of the subject invention address the need of the prior art for a reusable, disposable garment which exhibits good moisture vapor and air transmission, is soft, comfortable, quiet, easy to conform to the wearer's body.

Without further elaboration the foregoing will so fully illustrate my invention that others may, by applying current or future knowledge, adopt the same for use under various conditions of service.

I claim:

1. A disposable absorbent article arranged to be worn by a wearer to trap and collect liquid waste products of the wearer, said article comprising a flexible chassis having a front portion, a crotch portion, and a back portion, said front portion having a pair of breathable front side panels and a liquid-impervious central panel, said back portion having a pair of breathable back side panels and a liquid-impervious central panel, said chassis including a liquid absorbent layer, each of said back side panels having at least one fastening tab projecting therefrom, each of said fastening tabs having an adhesive surface, each of said front side panels being formed of a cloth-like material having an outer surface and at least one zone located on said outer surface, said zone comprising a single layer of a moisture impervious, tear-resistant, plastic film including a large plurality of small perforated apertures therein rendering said plastic film vapor-pervious, said plastic film having an outer surface and an inner surface, said inner surface of said plastic film being secured to said outer surface of a respective one of said side panels, said outer surface of said plastic film forming a release surface to which a respective one of said fastening tabs is arranged to be repeatedly adhesively releasably secured by said adhesive surface of said fastening tabs capable of holding said article in place on a wearer, said plastic film of each of said zones also making up a portion of said central panel of said front portion, said plurality of small apertures in said plastic film enabling moisture vapor from within said article to pass therethrough at a flow rate in the range of approximately 10 m3/m2.s to approximately 80 m3/m2.s per unit area of said plastic film, said plastic film being resistant to damage from repeated releasable securement of said fastening tabs thereto.

2. The disposable absorbent article of claim 1 wherein said at least one zone takes up a substantial area of said front waist portion.

3. The disposable absorbent article of claim 1 wherein said chassis comprises an outer cover, an inner liner, and said liquid absorbent layer, said liquid absorbent layer being interposed between said outer cover and said inner liner.

4. The disposable absorbent article of claim 3 wherein said outer cover comprises a soft non-woven hydrophobic material, and said inner liner comprises a soft non-woven hydrophilic material.

5. The disposable absorbent article of claim 4 wherein said liquid absorbent layer comprises cellulose pulp fibers.

6. The disposable absorbent article of claim 1 wherein said at least one zone is formed of plastic film having said release surface and wherein said fastening tab is arranged to be adhesively releasably secured to said release surface.

7. The disposable absorbent article of claim 1 wherein said chassis includes a inner liner, said inner liner being a soft hydrophilic material.

8. The disposable absorbent article of claim 1 wherein said front portion includes a waist section and said back portion includes a waist section and wherein at least one of said waist sections is elasticized.

9. The disposable absorbent article of claim 1 wherein said crotch portion of said chassis includes a pair of side recesses capable of receiving legs of a wearer.

10. The disposable absorbent article of claim 9 wherein said side recesses are elasticized.

11. The disposable absorbent article of claim 1 wherein said apertures are approximately 0.03 inch (0.76 mm) in diameter.

12. A disposable absorbent article arranged to be worn by a wearer to trap and collect liquid waste products of the wearer, said article comprising a flexible chassis having a front portion, a crotch portion, and a back portion, said chassis comprises an outer cover formed of a central panel and two pair of side panels comprising a front pair of side panels projecting outward from said central panel at said front portion and a back pair of side panels projecting outward from said central panel at said back portion, said central panel being a liquid-impervious laminate comprising a soft, cloth-like, hydrophobic layer on the outside and fluid-impervious film on the inside, each of said side panels being formed of a cloth-like, breathable, hydrophobic material having an outer surface, said chassis including a liquid absorbent layer, each of said side panels at said back portion having at least one fastening tab projecting therefrom, said outer surface of each of said side panels at said front portion comprising at least one zone formed of a single layer of a moisture impervious, tear-resistant, plastic film having an inner surface adhesively secured to said outer surface of a respective one of said side panels, said plastic film having an outer surface forming a release surface to which a respective fastening tab of said back portion is arranged to be releasably secured so as to be capable of holding said article in place on a wearer, said plastic film including a large plurality of small perforated apertures therein rendering said plastic film vapor-pervious to enable moisture vapor from within said article to pass therethrough at a flow rate in the range of approximately 10 m3/m2.s to approximately 80 m3/m2.s per unit area of said plastic film, said plastic film being resistant to damage from repeated releasable securement of said fastening tabs thereto.

13. The disposable absorbent article of claim 12 wherein said chassis includes a inner liner, said liner layer being a soft hydrophilic material.

14. The disposable absorbent article of claim 13 wherein said liquid absorbent layer is interposed between said outer cover and said inner liner.

15. The disposable absorbent article of claim 14 wherein said liquid absorbent layer comprises cellulose pulp fibers.

16. The disposable absorbent article of claim 8 wherein said article includes two zones and plural fastening tabs, at least one of said fastening tabs extending from one of said back pair of side panels and at least another of said fastening tabs extending from another of said back pair of side panels, and wherein each of said zones is located at said front portion and adapted to adhesively releasably receive a respective one of said fastening tabs.

17. The disposable absorbent article of claim 11 wherein said aperture are disposed in a staggered pattern spaced from one another by approximately 5 mm.

* * * * *